US006007335A

United States Patent [19]

Sheu

[11] Patent Number: 6,007,335

[45] Date of Patent: Dec. 28, 1999

[54] MEDICINE DISPENSER ADAPTED TO ADMINISTER LIQUID MEDICINE VIA A RETROMOLAR PAD AREA

[76] Inventor: Miin-Tchang Sheu, No. 156 Cheng Kung Road, Chang Hua City, Chang Hua Hsien, Taiwan

[21] Appl. No.: 09/166,915

[22] Filed: Oct. 6, 1998

[51] Int. Cl.[6] ................................ A61L 5/04; A61J 7/00; A61M 35/00

[52] U.S. Cl. ................................ 433/90; 604/77; 604/311

[58] Field of Search ................................ 433/80, 89, 90; 604/310, 311, 77

[56] References Cited

U.S. PATENT DOCUMENTS

| | | | |
|---|---|---|---|
| 1,588,846 | 6/1926 | McGreary | 215/11.1 |
| 2,816,547 | 12/1957 | Adisman | 215/11.1 |
| 3,572,337 | 3/1971 | Schunk | 604/77 |
| 4,127,126 | 11/1978 | Schunk | 604/77 |
| 4,276,880 | 7/1981 | Malmin | 433/80 |
| 4,569,662 | 2/1986 | Dragan | 433/89 |
| 4,758,158 | 7/1988 | Pierce et al. | 433/90 |
| 4,907,968 | 3/1990 | Eisner et al. | 433/80 |
| 4,993,941 | 2/1991 | Maita et al. | 433/80 |
| 5,244,388 | 9/1993 | Frush | 433/90 |
| 5,816,804 | 10/1998 | Fischer | 433/90 |

*Primary Examiner*—John J. Wilson
*Assistant Examiner*—Patrick A. Hilsmier
*Attorney, Agent, or Firm*—Bacon & Thomas

[57] ABSTRACT

A medicine dispenser adapted to administer liquid medicine via a retromolar pad area including a liquid collecting cylinder body and a soft plastic protective cover. The liquid collecting cylinder body includes a liquid discharge tube extending centrally from a top face thereof. The cylinder body is integrally formed with the liquid discharge tube, the latter having an open end at a top end. The protective tube has an internal hole matching the shape of the liquid discharge tube so that the latter can be fitted entirely into the internal hole of the protective tube. The deepest part of the internal hole of the protective tube is formed with a liquid discharge hole that is substantially at a right angle to the protective tube body so that liquid medicine flowing from the liquid discharge tube can bend at the rear section of the internal hole of the protective tube and out laterally from the liquid discharge hole. Hence, the direction of the discharge of the liquid medicine is in a parallel direction with the lateral direction of the subject's oral cavity. The liquid discharge tube is squeezed into the subject's mouth via a corner of the mouth and is entirely pushed into the oral cavity along the gap between the gums and the inner side of the cheek until the rear section of the liquid discharge tube is on one side of the retromolar pad area. Then the liquid medicine can be ejected laterally from the inwardly orienting lateral liquid discharge hole into the throat directly.

4 Claims, 2 Drawing Sheets

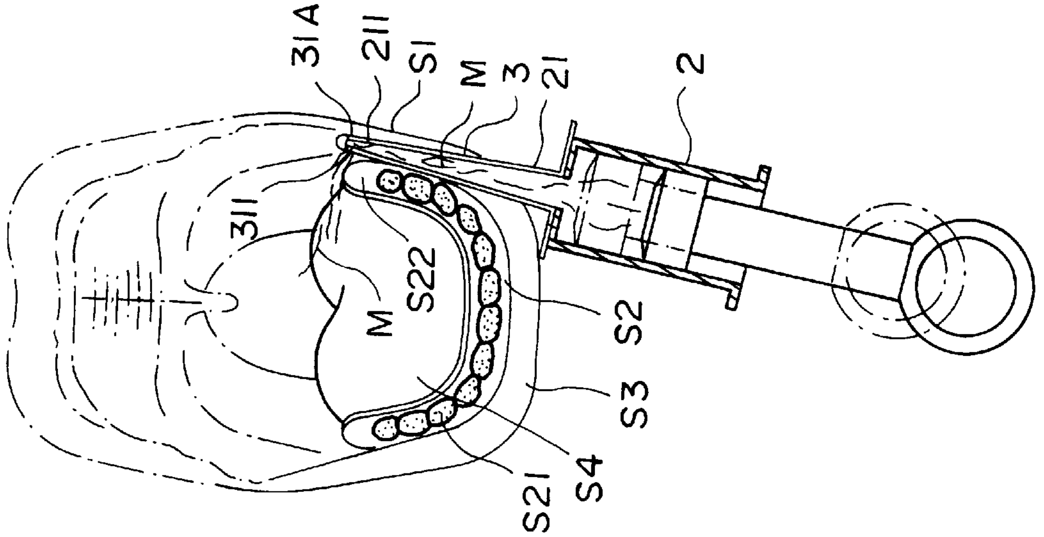
FIG3
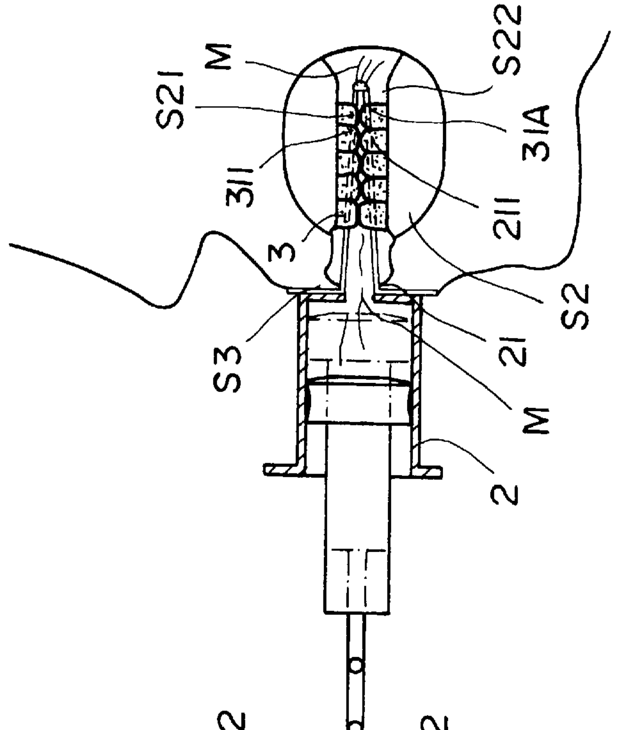
FIG4
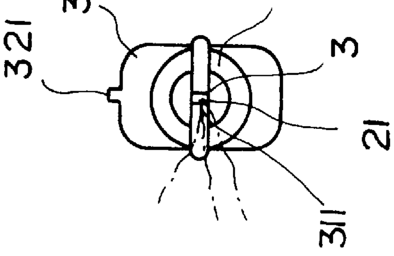
FIG4-A

MEDICINE DISPENSER ADAPTED TO ADMINISTER LIQUID MEDICINE VIA A RETROMOLAR PAD AREA

BACKGROUND OF THE INVENTION (a) Field of the Invention

The present invention relates generally to a medicine dispenser adapted to feed liquid medicine via a retromolar pad area, and more particularly to a medicine dispenser having a liquid discharge tube enveloped in a protective tube of soft plastic. The liquid discharge tube can be inserted into a subject's oral cavity from a comer of the mouth and be pushed further inwardly to its rear end until it is positioned naturally at the retromolar pad area at the rear sections of the gums so that liquid medicine can be ejected directly into the subject's throat, thus overcoming the problem of feeding subjects who are unwilling to open their mouth or who resist administration.

(b) Description of the Prior Art

Administering medicine to a subject who resists taking medicine and refuses to open his/her mouth is a very difficult job. In the past, some people would force open the subject's mouth and feed the medicine using a spoon. However, the subject might easily get choked by the medicine. There has been developed a kind of medicine dispenser that resembles a syringe, such as that disclosed in U.S. Pat. No. 4,127,126. However, as the medicine inevitably passes over the root of the tongue, the subject will likewise resist being fed the medicine.

There has also been developed a nipple-like medicine dispenser that has a Y-shaped liquid discharge passage, such that those taught in U.S. Pat. No. 2,816,547 and U.S. Pat. No. 1,588,846. In use, the medicine is ejected in two directions past the root of the tongue directly into the esophagus via the lateral sides of the throat, so that the subject will not taste the bitterness of the medicine.

However, after several trials, the subject will learn to resist the user's administration of medicine by shaking his/her head or refusing to open his/her mouth. Hence, the administration of medicine becomes difficult. Even if the user can force open the subject's mouth, the amount of the medicine dispensed cannot be easily controlled or the medicine will not flow along the expected path along the throat into the esophagus. And the subject, usually a baby, will feel more uncomfortable when tasting the bitter medicine and will resist administration even more violently.

In the above-mentioned medicine dispensing structures, they are also pushed to the central section of the oral cavity of the subject, and the subject needs to open his/her mouth to allow administration. If the subject refuses administration by clenching his/her teeth or gums or closing his/her mouth firmly, the user has to think of every means or require the help of another person to try to force open the subject's mouth, which is very troublesome and may hurt the subject. Furthermore, if the subject is a very small baby, clenching its gums firmly may hurt its gums or teeth or even its oral cavity.

SUMMARY OF THE INVENTION

The present invention takes into consideration the structure of the oral cavity of the human body and utilizes the "orifice" feature of the retromolar pad area as a passage for entry of liquid medicine.

A primary object of the present invention is to provide a medicine dispenser adapted to administer liquid medicine via the retromolar pad area. The medicine dispenser includes a liquid discharge tube enveloped by a protective tube of soft plastic. The liquid discharge tube can be squeezed into a subject's oral cavity on the inner side of the cheek from a corner of his/her mouth, and be pushed further inwardly to the rear section of the fornix of vestibule to be positioned naturally. The protective tube has an internal hole and a liquid discharge hole at a rear end of the internal hole. The liquid discharge hole is substantially at a right angle to the body of the protective tube and is substantially aligned with the side of the retromolar pad area at the rear section of the gums. As the subject cannot resist entry of the liquid discharge tube through the corner of the lips or the mouth by clenching his/her gums or teeth or using the force of his/her lower jaws, liquid medicine can be dispensed directly into the throat of the subject avoiding the taste buds and without the subject opening his/her mouth. Hence, medicine can be administered to the subject in a quick, convenient and safe manner, and the problem of the subject's resistance to administration can be overcome.

Another object of the present invention is to provide a medicine dispenser adapted to administer medicine via the retromolar pad area, in which as the liquid discharge tube fitted with a soft plastic protective tube is squeezed into the inner side of the cheek from the corner of the subject's mouth, it is held in position by the inner side of the cheek muscles and the outer side of the gums, so that administration of medicine can be smooth and precise.

A further object of the present invention is to provide a medicine dispenser adapted to administer medicine via the retromolar pad area, in which the liquid discharge tube squeezed into and held in position in the fornix of vestibule will not be obstructed by the clenching jaws of the subject. And even if the subject moves his/her tongue in resistance, it will not affect the administration of medicine from the liquid discharge tube. Moreover, as the subject will not feel entry of foreign object in his/her throat, he/she will not feel uncomfortable and is less likely to wiggle or resist administration. Besides, the liquid discharge tube will not hurt the subject's oral cavity.

BRIEF DESCRIPTION OF THE DRAWINGS

The foregoing and other features and advantages of the present invention will be more clearly understood from the following detailed description and the accompanying drawings, in which.

FIG. 3 is a schematic view illustrating use of the present invention in feeding medicine to a subject; and FIG. 4 is a schematic sectional view illustrating use of the present invention in feeding medicine to the subject; and FIG. 4A is a schematic view showing the identifying point on the stop face of the protective tube.

DETAILED DESCRIPTION OF THE PREFERRED EMBODIMENT

Figure 1:
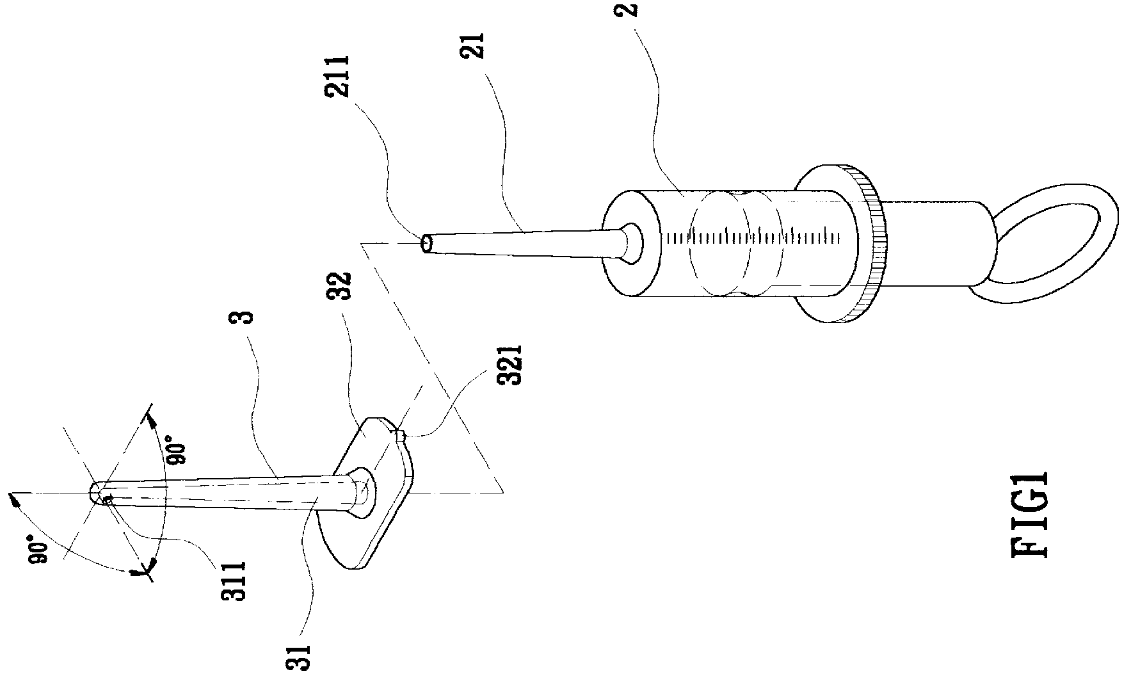
FIG. 1 is a perspective exploded view of the structure of the present invention.
Figure 2:
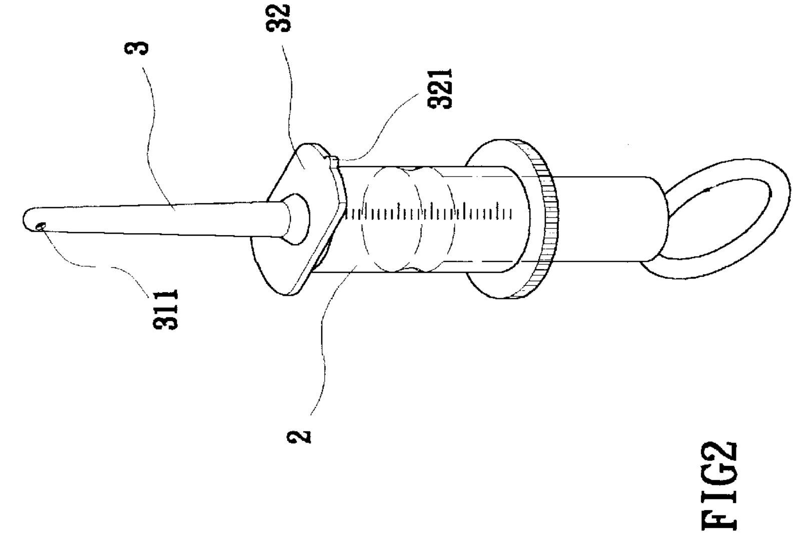
FIG. 2 is a perspective assembled view of the structure of the present invention.

With reference to FIGS. 1 and 2, the present invention comprises a liquid collecting cylinder body 2 for receiving and dispensing liquid medicine. A central section of the top face of the body 2 is provided with a liquid discharge tube 21 having a slender tube body that tapers upwardly. The liquid discharge tube 21 has a rear end forming an open end 211. There is further provided a soft plastic protective tube 3 that has an elongate internal hole 31 matching the shape and size of the liquid discharge tube 21 so that the entire liquid discharge tube 21 can be pushed into the protective tube 3. Hence, the entire discharge tube 21 is enveloped by the soft plastic protective tube 3.

The depth of the internal hole 31 of the protective tube 3 is slightly greater than the length of the liquid discharge tube 21. A side face of a rear section 31*a* of the internal hole 31 is provided with a liquid discharge hole 311 that is substantially at a right angle to the body of the protective tube 3. By means of the arrangement of the liquid discharge hole 311, liquid medicine M that comes from the liquid collecting cylinder body 2 towards the liquid discharge tube 21 and collected in the rear section 31A of the internal hole 31 of the protective tube can be compelled to "bend" and injected laterally from the liquid discharge hole 311.

A front section of the body of the protective tube 3 forms an enlarged stop face 32 adapted to serve as a positioning action element that stops at the front of the lip portion S3 of the subject to be fed. One side of the stop face 32 is protrudently provided with an identifying point 321 that is substantially at a right angle to the lateral direction of the liquid discharge hole 311. When the identifying point orients vertically upwardly, it indicates that the liquid discharge hole 311 is orienting towards the inner side in a horizontal position, thus allowing the user to identify easily and quickly the direction of the discharge of liquid medicine M.

Referring to FIGS. 3 and 4, the structure of the present invention is mainly directed to the following portions and features of the oral cavity of the human body:

1. Located between the inner side of the cheek S1 and the outer side of the gum S2, there is the fornix of vestibule, which is a flexible space. The fornix of vestibule does not appear to have any obvious space since the muscles of the cheek S1 normally rest against the outer side of the gum S2. However, due to the elasticity of muscles, when an external object (e.g., a toothbrush) is inserted into the fornix of vestibule, the inner side of the cheek S1 is pushed outwardly, forming an obvious cavity on the inner side of the cheek S1.
2. When we close our mouth, it is the lower jaw that bears the movement of the face muscles. When the subject to be fed closes his/her mouth, the closure and the clamping force formed by gun S2 and the teeth S21 thereon is very great (small babies will only have gums). If the user wants to ply open the subject's mouth when trying to feed him/her medicine, it will be very difficult unless the user presses or pinches the rear sections of both checks of the subject so that the subject feels painful and opens his/her mouth.
3. The outermost portions of the oral cavity are the lips S3 constituted by muscles. When the lips S3 are closed, since the lower jaw does not move, the closure S3 of the lips is controlled mainly be the muscles around the lips S3, and the closure force is therefore not great. Besides, as the lips S3 are formed by soft muscles, it is easy to open the lips from the upper and lower portion of the lips or corners of the mouth to make an opening.
4. There is a retromolar pad area at the innermost sections of the upper and lower gums S2 of the oral cavity. When the mouth is closed, the upper and lower gums S2 forms an "orifice" of a width about 1 cm at the innermost section of the upper and lower gums S2 at the retromolar pad area. The orifice is substantially located at the inner side in front of the rear section of the fornix of vestibule.

Based on the above-mentioned features of the structure of the oral cavity of the human body, the user may ply open the corner of the lips S3 of the subject with relative ease and insert the liquid discharge tube 21 fitted with the soft plastic protective tube 3 into the oral cavity and, using the identifying point 321 on the stop face 32 at the front section of the protective tube 3 to assist proper alignment, causes the liquid discharge hole 311 to face inwardly in a lateral direction so that the lateral direction of the oral cavity of the subject is in a "parallel" state as shown in FIG. 4A. The user may then insert the entire section of the liquid discharge tube 21 into the inner side of the cheek S1 and push further inwardly until the laterally orienting liquid discharge hole 311 extending on the side of the retromolar pad area S22 at the innermost side of the gums S2 is stopped and positioned. Then the user may feed the liquid medicine M from the liquid collecting cylinder body 2 so that the liquid medicine M is ejected sideways and laterally from the liquid discharge hole 311. At this point, since the liquid discharge tube 31 fitted with the soft plastic protective tube 3 slants slightly outwardly due to the slight enlargement of the rear section of the gums S2, the liquid discharge hole 311 that is originally at a right angle to the body of the tube slants slightly so that it faces the fauces at the inner most portion of the oral cavity (see FIG. 3). At this time, the liquid medicine M can be directly injected into the throat into the esophagus, avoiding the taste buds on the tongue S4, or along the walls of the throat into the esophagus. In this way, liquid medicine can be fed to a subject quickly, easily, and safely without having to force the subject to open his/her mouth.

Furthermore, since the liquid discharge tube 21 fitted with the soft plastic protective tube 3 is located in the fornix of vestibule at the inner section of the cheek S1 between the inner side of the muscles of the cheek S1 and the outer side of the gums S2, it is supported and positioned on both sides so that liquid medicine M can be fed in a relatively precise and stable manner.

In summary, the present invention provides a liquid medicine dispenser that can be extended into the oral cavity of the subject from the corner of the mouth without having to force the subject to open his/her mouth. The present invention makes feeding of liquid medicine to subjects relatively easy, quick and convenient.

Although the present invention has been illustrated and described with reference to the preferred embodiment thereof, it should be understood that it is in no way limited to the details of such embodiment but is capable of numerous modifications within the scope of the appended claims.

What is claimed is:

1. A medicine dispenser adapted to administer liquid medicine via a retromolar pad area, comprising a liquid collecting cylinder body for receiving and supplying liquid medicine, said cylinder body having a liquid discharge tube extending centrally from a top face thereof, said liquid discharge tube having a rear end forming an open end and a slender tube body that tapers towards said rear end; and a soft plastic protective tube that has an elongate internal hole that matches the shape of said liquid discharge tube so that said liquid discharge tube can be fitted entirely into and enveloped by said protective tube, wherein said internal hole of said protective tube is slightly greater than said liquid discharge tube and is formed with a liquid discharge hole at one side of a rear section thereof, said liquid discharge hole being substantially at a right angle to said protective tube, thereby defining a retromolar dispensing tube so that liquid medicine from said liquid collecting cylinder body to said liquid discharge tube flowing to the rear section of said internal hole of said protective tube bends at said liquid discharge hole and out in a lateral direction; and said protective tube has a front section of its body forming an enlarged stop face that stops at the lips portion of a subject to be fed, said stop face having a projecting identifying point on one side thereof, said identifying point being substantially at a right angle to the lateral direction of said liquid discharge hole, whereby when said identifying point is vertical and orients upwardly, it indicates that said liquid discharge tube is horizontal and orients inwardly, thus providing the user a quick and convenient way to identify the direction of discharge of liquid medicine; whereby said liquid discharge tube fitted with said soft plastic protective tube can be squeezed into the inner side of the cheek of the subject from a corner of the mouth and pushed further inwardly to a position where said liquid discharge tube is stopped, and the liquid medicine is fed via the retromolar pad area at the rear section of the gums in the oral cavity into the throat.

2. A method for orally administering a liquid medication to an individual while said individual's jaws are clenched which comprises introducing the dispenser of claim 1 between the lips of said individual; pushing said discharge tube inwardly to the rear section of the individual's fornix of vestibule; aligning said liquid discharge hole so that it faces the retromolar pad area of said individual; and passing said liquid medication through said liquid discharge hole whereby said liquid passes across the retromolar pad area of the individual into the individual's throat while the jaws of said individual are clenched.

3. The medicine dispenser of claim 1 which has a single liquid discharge hole.

4. A method for orally administering a liquid medication to an individual while said individual's jaws are clenched which comprises introducing the dispenser of claim 2 between the lips of said individual; pushing said discharge tube inwardly to the rear section of the individual's fornix of vestibule; aligning said liquid discharge hole so that it faces the retromolar pad area of said individual; and passing said liquid medication through said liquid discharge hole whereby said liquid passes across the retromolar pad area of the individual into the individual's throat while the jaws of said individual are clenched.

* * * * *